US009700263B2

(12) United States Patent
Patel

(10) Patent No.: US 9,700,263 B2
(45) Date of Patent: Jul. 11, 2017

(54) ELECTRONIC PHYSICAL THERAPY AND REHABILITATION ROLLING DEVICE WITH TACTILE SENSOR ARRAY

(71) Applicant: Tarak Dolat Patel, Tampa, FL (US)

(72) Inventor: Tarak Dolat Patel, Tampa, FL (US)

(*) Notice: Subject to any disclaimer, the term of this patent is extended or adjusted under 35 U.S.C. 154(b) by 66 days.

(21) Appl. No.: 14/723,383

(22) Filed: May 27, 2015

(65) Prior Publication Data
US 2015/0265871 A1    Sep. 24, 2015

(51) Int. Cl.
*A61B 5/00* (2006.01)
*A61H 15/00* (2006.01)
(Continued)

(52) U.S. Cl.
CPC ............ *A61B 5/748* (2013.01); *A61B 5/0004* (2013.01); *A61B 5/0022* (2013.01); *A61B 5/0402* (2013.01); *A61B 5/0476* (2013.01); *A61B 5/0488* (2013.01); *A61B 5/1118* (2013.01); *A61B 5/6895* (2013.01); *A61H 15/00* (2013.01); *A61B 2505/09* (2013.01); *A61H 2015/0014* (2013.01); *A61H 2201/1695* (2013.01); *A61H 2201/5002* (2013.01); *A61H 2201/5012* (2013.01); *A61H 2201/5061* (2013.01); *A61H 2201/5064* (2013.01); *A61H 2201/5069* (2013.01); *A61H 2201/5071* (2013.01); *A61H 2201/5082* (2013.01); *A61H 2201/5084* (2013.01); *A61H 2201/5092* (2013.01); *A61H 2201/5097* (2013.01); *A61H 2230/04* (2013.01); *A61H 2230/10* (2013.01); *A61H 2230/60* (2013.01); *A61H 2230/65* (2013.01); *A63B 21/0004* (2013.01); *A63B 21/0552* (2013.01); *A63B 21/4033* (2015.10); *A63B 21/4035* (2015.10); *A63B 21/4049* (2015.10); *A63B 23/0205* (2013.01); *A63B 71/0619* (2013.01); *A63B 2023/006* (2013.01); *A63B 2209/10* (2013.01); *A63B 2220/10* (2013.01); *A63B 2220/18* (2013.01); *A63B 2220/40* (2013.01); *A63B 2220/51* (2013.01); *A63B 2220/54* (2013.01); *A63B 2220/56* (2013.01); *A63B 2220/72* (2013.01); *A63B 2220/74* (2013.01); *A63B 2220/806* (2013.01); *A63B 2220/807* (2013.01); *A63B 2225/15* (2013.01);
(Continued)

(58) Field of Classification Search
None
See application file for complete search history.

(56) References Cited

U.S. PATENT DOCUMENTS

| 6,368,251 B1 * | 4/2002 | Casler ................. A63B 21/005 482/4 |
| 2006/0047538 A1 * | 3/2006 | Condurso ............ G06F 19/326 705/3 |

(Continued)

*Primary Examiner* — Sundhara Ganesan

(57) ABSTRACT

A touch screen based exercise roller device is disclosed. The device comprising an elongated, cylindrical shell configured to support physical activity of a user, a processing unit, a sensor array for measurement data associated with at least one parameter associated with physical activity, wherein the sensor array linked to the processing unit, and a touch screen attached onto the outer surface of the shell communicatively linked for controlling a software application, wherein the software application is configured to process data associated with the physical activity of a user.

11 Claims, 6 Drawing Sheets

(51) Int. Cl.
*A61B 5/11* (2006.01)
*A61B 5/0476* (2006.01)
*A61B 5/0402* (2006.01)
*A61B 5/0488* (2006.01)
*A63B 71/06* (2006.01)
*A63B 21/00* (2006.01)
*A63B 23/00* (2006.01)
*A63B 21/055* (2006.01)
*A63B 23/02* (2006.01)

(52) U.S. Cl.
CPC ....... *A63B 2225/50* (2013.01); *A63B 2225/54* (2013.01); *A63B 2230/04* (2013.01); *A63B 2230/10* (2013.01); *A63B 2230/60* (2013.01); *A63B 2230/65* (2013.01)

(56) References Cited

U.S. PATENT DOCUMENTS

| | | | | |
|---|---|---|---|---|
| 2008/0273008 | A1* | 11/2008 | Chang | A61H 15/00 345/156 |
| 2010/0130333 | A1* | 5/2010 | Strong | A63B 69/004 482/83 |
| 2010/0240495 | A1* | 9/2010 | Law | A63B 21/0004 482/9 |
| 2012/0021873 | A1* | 1/2012 | Brunner | A63B 24/0075 482/9 |
| 2012/0071732 | A1* | 3/2012 | Grey | G06F 19/3481 600/301 |
| 2014/0088995 | A1* | 3/2014 | Damani | G06F 19/3418 705/2 |
| 2014/0371784 | A1* | 12/2014 | Kwak | A61H 39/04 606/204 |
| 2016/0279018 | A1* | 9/2016 | Egan | A61H 15/02 |

* cited by examiner

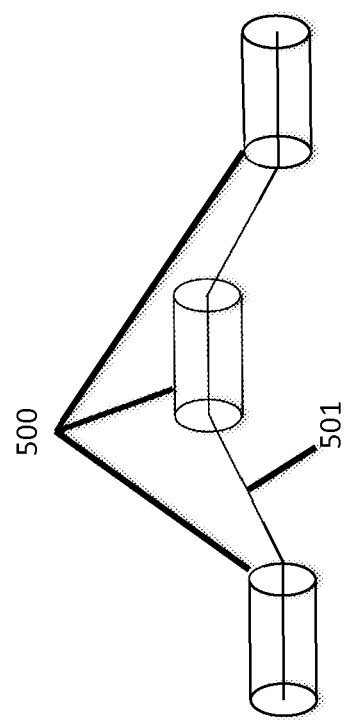

ELECTRONIC PHYSICAL THERAPY AND REHABILITATION ROLLING DEVICE WITH TACTILE SENSOR ARRAY

COPYRIGHT & TRADEMARK NOTICES

A portion of the disclosure of this patent document may contain material, which is subject to copyright protection. Certain marks referenced herein may be common law or registered trademarks of the applicant, the assignee or third parties affiliated or unaffiliated with the applicant or the assignee. Use of these marks is for providing an enabling disclosure by way of example and shall not be construed to exclusively limit the scope of the disclosed subject matter to material associated with such marks.

BACKGROUND OF THE INVENTION

The present invention relates to exercise rollers with structural conversion capabilities while embedded with an integrated technological interface and telemetry data systems that is used for exercise and myofascial release.

General Background and State of the Art

Exercise rollers are ubiquitous in the physical therapy, sports medicine and in the exercise training world. The primary purpose of exercise rollers is to inhibit overactive muscle tension by stretching the muscle fibers through autogenic inhibition.

These instruments help lengthen short or tight muscles, tendons and ligaments. Some muscles including psoas major, illiacus, rectus femoris, pectinus and sartorious and the iliotibial band, a tendon that connects the hip muscles to the knee. Frequently, the roller is used in increments of 30-60 sec. under the painful areas commonly referred to as Trigger Points or Trps.

These devices are commonly found in 12" lengths with 6" diameters, however 36" lengths are avaiable to accommodate larger muscle areas in dorsal side of the body. They are either composed of polyethylene foam or EVA foam. Most do not have a non-slip surface to ameliorate friction between the user and the most superficial layer of the foam layer. Consequently, the user can slip on the exercise roller when moving back and forth.

Abdominal rollers are common in most gyms as a choice for achieve core strength in the pelvic or hip region of the body, not the so much the abdominal muscles as the name would indicate. Most are composed of a plastic wheel(s) with a metal handle on either side to grasp onto. However, most have a narrow grip which target different areas of the back, contrary to a wider grip which hits a disparate section of the back.

Though using the abdominal roller requires the use of several muscle groups, it primarily targets your iliopsoas muscles, which are found deep in the pelvic region or hips. This muscle is made up of two parts named the iliacus and psoas. The common term for this muscle is hip flexor and, as its name indicates, it is used during flexion of the hip. The rectus abdominis and oblique muscles, which are found in the lower abdomen and sides of your torso, respectively, contract to stabilize your torso while you push the abdominal roller away from the knees. Due to the narrow grip, the contraction of the latissimus dorsiis on the inferior end as it is pulled back toward the body.

There is a need for exercise rollers with a rubber outer surface to decrease the chance of slipping while rolling. Moreover, the exercise roller should be convertible into another similar or complementary device, the wide grip abdominal roller. This capability is required as it creates more value for the consumer. There is a need for a technological interface, which will utilize various external medical hardware to essentially locate pain in a shorter period of time, hence speeding up the recovery process for patients in discomfort while transmitting the data through telemetry data systems to their healthcare provider.

There is a need for roller devices to be able to track and analyze data more accurately for device user or patient users.

SUMMARY OF THE INVENTION

It is an object of the present invention to provide a multidimensional device with a multitude of capabilities that will help users to achieve pain relief through precise locators for pain through the use of sensors, electrodes and probes. The data is then relayed through the telemetry system.

Another object of the present invention is to provide users an alternative therapeutic device, specifically a wide grip abdominal roller. Structural changes can be made by inserting a cylindrical rod through the center point of the foam cylinder to convert the device into a wide grip abdominal roller.

In an embodiment, the roller device comprises at least one physiological sensor for measuring at least one physiological parameter. In such an embodiment, data collected from a physiological sensor enabled in the device could provide vital health information, wherein such information could be transmitted via a network, such as the Internet, a body area network (BAN), a local area network (LAN), a wireless network, to a software application associated with the device, wherein the data could be received by one or more servers associated with a user identification, wherein the user can be a user of the device, or a health care provider, which has at least one health information system, wherein one user is a patient associated with a patient identifier and another user is a health care provide, such as a physician, nurse, therapist, etc.

In one embodiment, the roller device includes at least one muscle sensor, or a capacitive pressure sensor for measuring muscle motion or activities. Such a capacitive sensor would preferably be bendable or flexible so that, for example, an array of pressure sensors can be built into the outer layer of the roller, for providing adequate performance in rolling the device.

In one embodiment, the roller device is configured to interface with at least one wearable device containing sensors. These sensors can be incorporated or woven into the fabric that register the electrical excitation of the muscle fibers, and thin conducting metallic fibers that conduct the signals to an electronic analysis system.

In one embodiment, the roller device consists of a sensor for detecting muscle pain stemming from muscular TrPs or Trigger Points through the use of interferential currents; this is the putative source of pain most referenced by studies of clinical muscle pain. Although, the standard is to use palpation with pressure to locate TrPs, it has been proven unreliable for detecting taut bands and local twitch response.

In one embodiment, the roller device can be used with a cylindrical metal rod that can be inserted through the center of the foam cylinder to convert the exercise roller into a wide grip abdominal roller.

In another embodiment, the roller device comprises at least one detachable portion for use in various portions of a user's body.

In another embodiment, the roller device is a reconfigurable roller device that can a plurality of different shapes aside from a standard configuration.

In another embodiment, the roller device is reconfigurable with at least two reconfigurable portions roller device that can be reconfigured with a plurality of different shapes aside from a standard configuration.

BRIEF DESCRIPTION OF THE DRAWINGS

FIG. 5 depicts an exemplary embodiment of a roller device that is reconfigurable.

DETAILED DESCRIPTION

Figure 1:
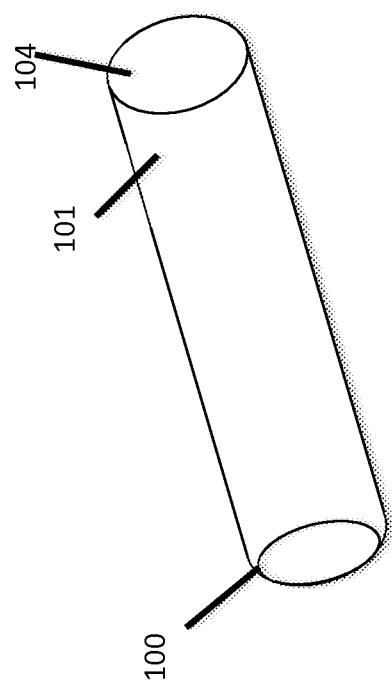
FIG. 1 depicts a perspective view of an embodiment of the roller device.

FIG. 1 depicts a perspective view of an embodiment of the roller device 100. The roller device 100 is comprised of at least an outer surface 101 and an inner surface 104 of a preferably elongated cylindrical shell suitable for rolling in exercise or physical activity. The device 100 may be comprised of material foam, such as high density foam, polyethylene foam or other compressible material known in the art of roller devices created for physical fitness and exercise. Alternatively, inner surface may comprise an interior cylindrical form for greater hardness felt by a user of the device 100, which is comprised of plastic or metal. The outer surface 101 is preferably made from rubber or one or more other materials suitable for physical contact with humans. Preferably, the general shape of the roller device 100 is one that is elongated and cylindrical, as generally found in the art. Moreover, the length and diameter of the roller device 100 may be of any dimensions, but is preferably of the size of roller devices known in the art. Roller device 100 of FIG. 1 provides a more general view of various embodiments described throughout the description below and figures.

Figure 2:
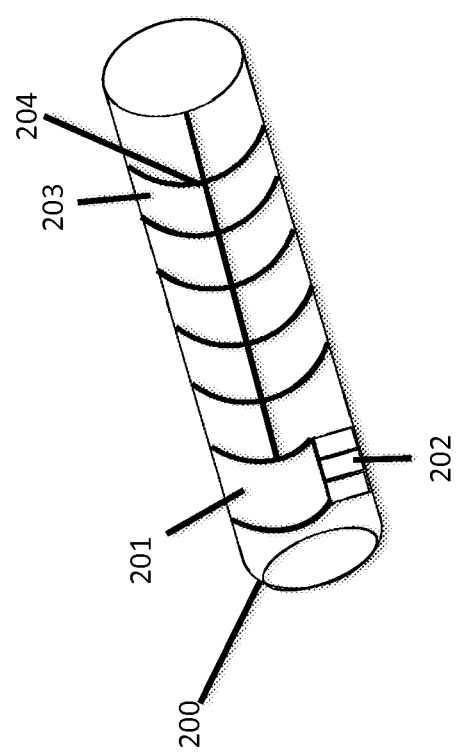
FIG. 2 depicts a perspective view of an embodiment of the roller device with a pressure sensor array and touch screen for control.

FIG. 2 depicts a perspective view of an embodiment of the roller device 200 with a pressure sensor array 204 and transparent touch screen 201 for control and display, including at least two buttons 202 for aiding in the control and operation of the roller device 200. The pressure or tactile sensor 203 may be one or more different types of tactile sensors 203 arrange as an array 204 around the outer surface of the roller device 200. Touch screen 201 may be resistive, capacitive, including surface and projected capacitive, surface acoustic wave, or infrared and can be further comprised of one or more materials for providing flexibility and durability for normal use of the roller device 200. Tactile sensors 203 used in the array may include piezoresistive, piezoelectric, capacitive, pressure, and elastoresistive sensors. Other forms of sensors that can implemented in the device include muscle activity sensors, electromyography sensors, electroencephalography sensors, and electrocardiography sensors.

In one embodiment, the touch screen 201 may control a software application which provides an instructional video on the screen for a user of the device 200 to view various sequences of device 200 operation. For example, various sequences of operation of the device 200 would result in an exercise engaging at least one muscle of a user. The software application can be connected to a network such as the Internet wherein the instructions on how to perform various exercises available to a user of the device 200 are updated from a database by the device 200.

In another embodiment, the touch screen 201 can cover all or most of the outer surface of the device 200 to allow for the use of touch screen technology in measuring and capturing data related, to the exercise activity associated with a user of the device 200.

Far beyond what is currently available in the current innovations of exercise rolling devices, in another embodiment, the pressure sensors 203 form an array 204, wherein different segments of the array can measure the pressure applied to the sensors 203 in that segment. Such measurements can then be interpreted as signals by the software application associated with the device 200 to create a body mapping software application associated with the device 200, wherein the amount of pressure as measured by the sensors in various segments of the sensor array are visually rendered on the screen.

Visual rendering on a body map can be done either as a step after the session with the device 200 is complete, by the user, or else, can be automated by the use of video camera technology. In an embodiment, where the body map is generated automatically, a video camera based system using video gesture recognition may be used to get at least the outline of the shape of the body part on which the roller is to be applied. A gesture recognition module, linked to a processing unit can then recognize body parts of a user of the device 200. The user can then apply the roller device 200 for normal use.

In another embodiment, the segments on the sensor array 204 are lighted wherein different colored lighting is used to indicate variations in the amount of pressure applied by a user of the device 200.

Figure 3:
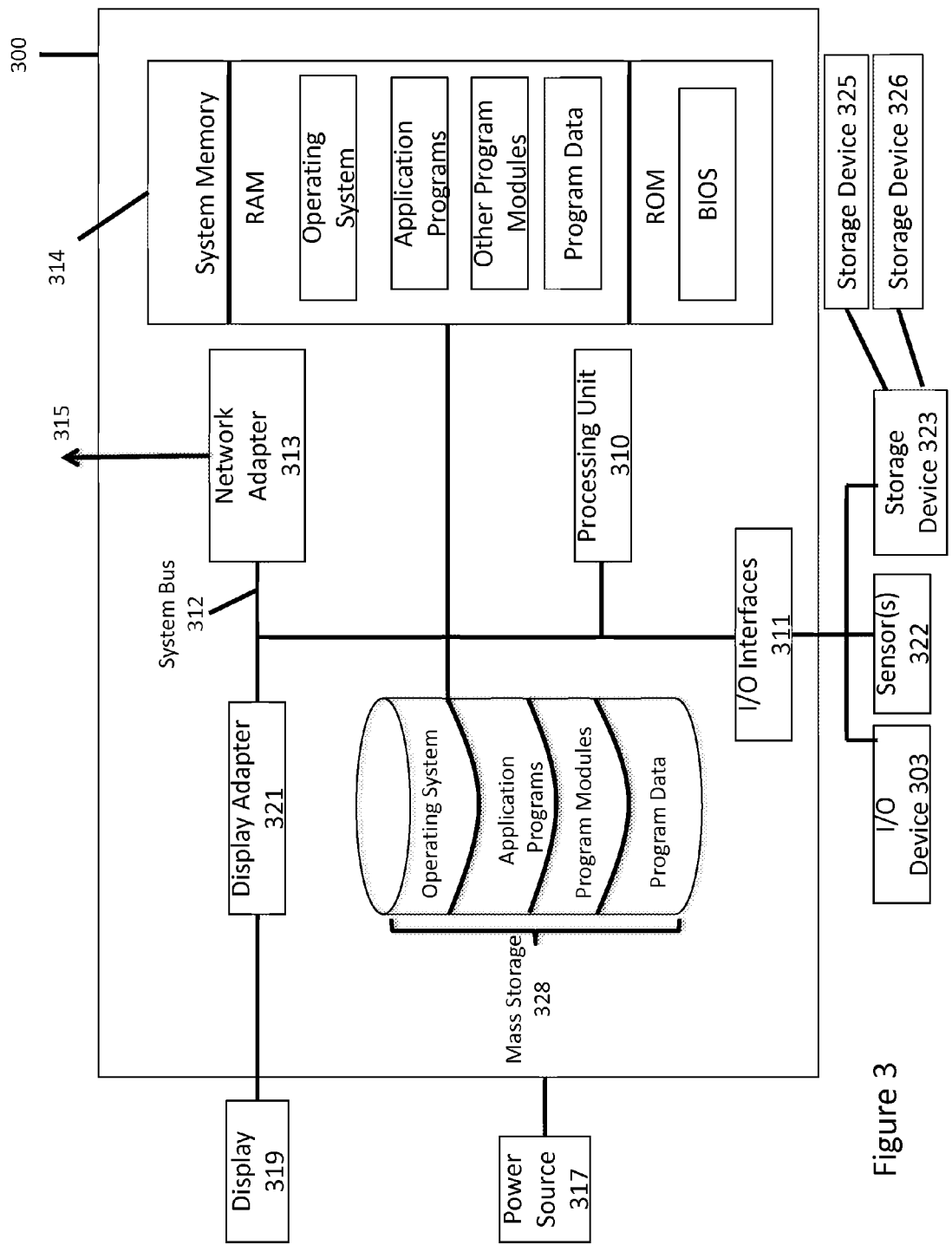
FIG. 3 is a block diagram showing an exemplary computing environment in which the technologies described herein can be implemented based on one or more embodiments.

FIG. 3 is a block diagram showing an exemplary computing environment in which the technologies described herein can be implemented based on one or more embodiments. Specifically, such an embodiment depicts software and hardware components in a computing environment. A suitable computing environment can be implemented with systems including but are not limited to, smart devices, microprocessor-based systems, multiprocessor systems, servers, workstations, etc.

Computing environment typically includes a general-purpose computing system in the form of a computing device 300 coupled to various components, such as peripheral devices 323, 325, 326 and the like. Computing device 300 can couple to various other components, such as input devices 306, including voice recognition, touch pads, buttons, keyboards and/or pointing devices, such as a mouse or trackball, via one or more input/output ("I/O") interfaces 311. The components of computing device 200 can include one or more processors (including central processing units ("CPU"), graphics processing units ("GPU"), microprocessors ("UP"), and the like) 310, system memory 314, and a system bus 312 that typically couples the various components. Processor 310 typically processes or executes various computer-executable instructions to control the operation of computing device 300 and to communicate with other electronic and/or computing devices, systems or environment (not shown) via various communications connections such as a network connection 315 or the like. System bus 312 represents any number of several types of bus structures, including a memory bus or memory controller, a peripheral bus, a serial bus, an accelerated graphics port, a processor or local bus using any of a variety of bus architectures, and the like.

System memory 314 can include computer readable media in the form of volatile memory, such as random access memory ("RAM"), and/or nonvolatile memory, such as read only memory ("ROM") or flash memory ("FLASH"). A basic input/output system ("BIOS") can be stored in non-volatile or the like. System memory 314 typically stores data, computer-executable instructions and/or program modules comprising computer-executable instructions that are immediately accessible to and/or presently operated on by one or more of the processors 310. Mass storage devices 323 and 328 can be coupled to computing device 300 or incorporated into computing device 300 via coupling to the system bus 312. Such mass storage devices 323 and 328 can include non-volatile RAM, a magnetic disk drive which reads from and/or writes to a removable, non-volatile magnetic disk 325, and/or an optical disk drive that reads from and/or writes to a non-volatile optical disk such as a CD ROM, DVD ROM 326. Alternatively, a mass storage device 328, such as hard disk 328, can include non-removable storage medium. Other mass storage devices 328 can include memory cards, memory sticks, tape storage devices, and the like. Mass storage device 328 can be remotely located from the computing device 300.

Any number of computer programs, files, data structures, and the like can be stored in mass storage 328, other storage devices 323, 325, 326 and system memory 314 (typically limited by available space) including, by way of example and not limitation, operating systems, application programs, data files, directory structures, computer-executable instructions, and the like.

Output components or devices, such as display device 319, can be coupled to computing device 300, typically via an interface such as a display adapter 321. Output device 319 can be a liquid crystal display ("LCD"). Other example output devices can include printers, audio outputs, voice outputs, cathode ray tube ("CRT") displays, tactile devices or other sensory output mechanisms, or the like. Output devices can enable computing device 300 to interact with human operators or other machines, systems, computing environments, or the like. A user can interface with computing environment via any number of different I/O devices 303 such as a touch pad, buttons, keyboard, mouse, joystick, game pad, data port, and the like. These and other I/O devices 303 can be coupled to processor 310 via I/O interfaces 311 which can be coupled to system bus 312 and/or can be coupled by other interfaces and bus structures, such as a parallel port, game port, universal serial bus ("USB"), fire wire, infrared ("IR") port, and the like.

The computing environment of FIG. 3 can also include sensor(s) 322. Example sensor(s) 322 include, inter alia, include a: GPS, accelerometer, inclinometer, position sensor, barometer, WiFi sensor, radio-frequency identification (RFID) tag reader, gyroscope, pressure sensor, pressure gauge, time pressure gauge, torque sensor, infrared image capture device, ohmmeter; thermometer, microphone, image sensor (e.g. digital cameras), biosensor (e.g. photometric biosensor, electrochemical biosensor), capacitance sensor, radio antenna, augmented reality camera, capacitance probe, proximity card reader, electronic product code reader, any other detection technology, or any combination thereof. It should be noted that the other sensor devices other than those listed can also be utilized to sense context information.

Computing device 300 can operate in a computing environment via communications connections to one or more remote computing devices through one or more cellular networks, wireless networks, local area networks ("LAN"), wide area networks ("WAN"), storage area networks ("SAN"), the Internet, radio links, optical links and the like. Computing device 300 can be coupled to a network via network adapter 313 or the like, or, alternatively, via a modem, digital subscriber line ("DSL") link, integrated services digital network ("ISDN") link, Internet link, wireless link, or the like.

Communications connections, such as a network connection 315, typically provides a coupling to communications media, such as a network. Communications media typically provide computer-readable and computer-executable instructions, data structures, files, program modules and other data using a modulated data signal, such as a carrier wave or other transport mechanism. The term "modulated data signal" typically means a signal that has one or more of its characteristics set or changed in such a manner as to encode information in the signal. By way of example, and not limitation, communications media can include wired media, such as a wired network or direct-wired connection or the like, and wireless media, such as acoustic, radio frequency, infrared, or other wireless communications mechanisms.

Power source 317, such as a battery or a power supply, typically provides power for portions or all of computing environment. In the case of the computing environment being a mobile device or portable device or the like, power source 317 can be a battery. Alternatively, in the case that the computing environment is a smart device or server or the like, power source 317 can be a power supply designed to connect to an alternating current (AC) source, such as via a wall outlet.

Some computers, such as smart devices, may not include several of the components described in connection with FIG. 3. For example, a smart device may not include a user interface. In addition, an electronic badge can be comprised of a coil of wire along with a simple processing unit 310 or the like, the coil configured to act as power source 317 when in proximity to a card reader device or the like. Such a coil can also be configure to act as an antenna coupled to the processing unit 310 or the like, the coil antenna capable of providing a form of communication between the electronic badge and the card reader device. Such communication may not involve networking, but can alternatively be general or special purpose communications via telemetry, point-to-point, RF, infrared, audio, or other means. An electronic card may not include display 319, I/O device 303, or many of the other components described in connection with FIG. 3. Other devices that may not include some of the components described in connection with FIG. 3, include electronic bracelets, electronic tags, implantable devices, computer goggles, other body-wearable computers, smart cards and the like.

Figure 4A:
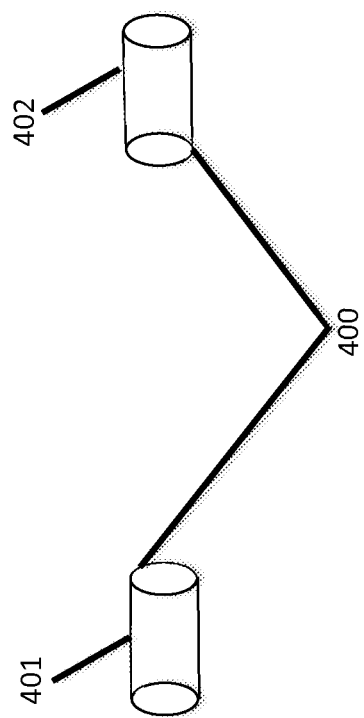
FIGS. 4a-4b illustrate various exemplary embodiments of a roller device.
Figure 4B:
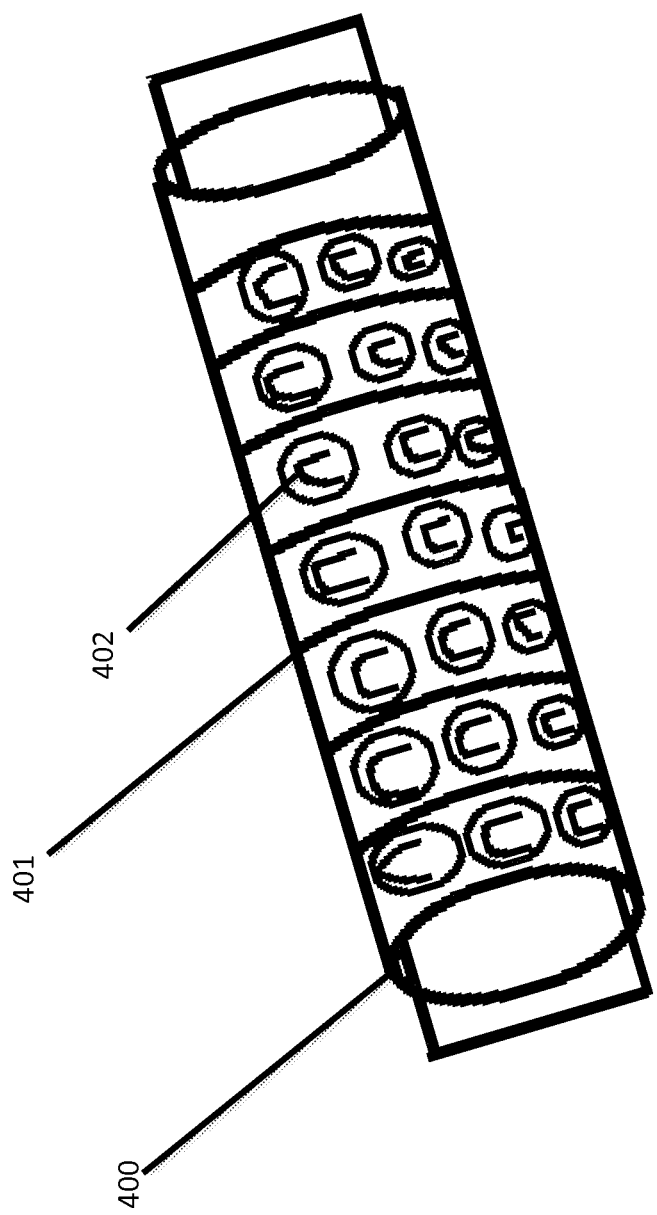

FIG. 4a illustrates an exemplary embodiment of a roller device 400 with at least one detachable portion 401, 402. The detachable portion can be of various types. In one embodiment, at least one detachable portion 401, 402 of the roller device 400 can be detached by pressing a release button which releases a latch holding the detachable portions together. The latch can easily be re-engaged to use the roller device as a single piece rather than a plurality of pieces. Having detachable portions 401, 402 can still allow all portions of the device to be networked either by a wired or wireless link, such that the software application and touch screen 201 hardware associated with the device can communicate with all portions of the device. Having detachable portions allows for a wider range of exercises to be performed as well as provides a smaller portion of the device 400 to be configured for use with certain hard to reach or difficult to stretch muscle groups.

Other forms of attaching and detaching portions of the roller device 400 can include Velcro, hooks, fasteners, clips, buckles, and the like. Furthermore, in certain embodiments, an opening through the core of the inner surface 104 of the roller device 100. Variations of these embodiments allow for coupling resistance bands to various parts of the roller device such as through the cross section of the exercise roller.

FIG. 4a illustrates an exemplary embodiment of a roller device 400 with circumferential crevasses 401 for more air flow between a user's body and the device 400 and massage ridges 402 on the outer surface of the device 400 for variation in exercise activity.

FIG. 5 depicts an exemplary embodiment of a roller device 500 that is reconfigurable. Specifically, in an embodiment where the roller device 500 is reconfigurable, electronically configured using robotics 501. Robotics 501 can include reconfigurable robotics 501 such as self-reconfigurable modular robotics, which can include can contain electronics, sensors, computer processors, memory, and power supplies.

In an exemplary embodiment of a software application configured to control an embodiment of the roller device 100. For example, the software application associated with the device can be linked to a health information system and a electronic medical record system, wherein a physical therapist or other health care professional may prescribe one or more regimens for exercise and therapy for a patient user, wherein the user is either remotely located or within a clinical setting, such as a hospital or physical therapy clinic.

In another embodiment, a module associated with the software application of the device allows for a health care provider to prescribe or customize a regimen for providing health care, including at least one activity associated with physical therapy and rehabilitation associated with a patient user. For example, a health care provider such as a physical therapist can select a condition for the patient and begin an ongoing prescription workflow. For example, the physical therapist may prescribe doing shoulder related exercises that require less physical exertion; however, the software associated with the system can collect and interpret measured data from the user, such as the data from the pressure sensor arrays on the outer surface of the data. Data can include but is not limited to pressure sensor data, dates and times and duration of use by the user, pain or tension related data, messages or responses to questions which can be programmed manually or dynamically changed based upon previously provided data or responses, and the like. This data can then be used to trigger one or more different prescriptions or recommendations for further exercises to do in order to optimize care. For example, in one embodiment, pain data or tension data can be assessed on a predetermined scale or a newly created scale automatically by the software application based on historical data from a particular user, such an assessment can be related to severity of the pain or tension and subsequently, the software application associated with the device can provide a medical diagnosis, treatment options, and prescription of pain medication or prescription of certain physical therapy or rehabilitation regimens. Such a feature of using user data to trigger workflow allows for the personalization of care and rehabilitation, which is clearly lacking in today's market of roller devices.

In another embodiment, the device can be configured via the processing unit and other computing environment hardware to link with a wearable device. Such a wearable device may be for measuring, tracking, and communicating parameters of physical activity, such as that created by FitBit Inc., Apple Inc., and the like known in the art.

Closing Remarks

The terms "certain embodiments", "an embodiment", "embodiment", "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

While the invention has been described in detail with reference to disclosed embodiments, various modifications within the scope of the invention will be apparent to those of ordinary skill in this technological field. It is to be appreciated that features described with respect to one embodiment typically can be applied to other embodiments.

The invention can be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

Although exemplary embodiments have been provided in detail, various changes, substitutions and alternations could be made thereto without departing from spirit and scope of the disclosed subject matter as defined by the appended claims. Variations described for the embodiments may be realized in any combination desirable for each particular application. Thus particular limitations and embodiment enhancements described herein, which may have particular advantages to a particular application, need not be used, for all applications. Also, not all limitations need be implemented in methods, systems, and apparatuses including one or more concepts described with relation to the provided embodiments. Therefore, the invention properly is to be construed with reference to the claims.

I claim:

1. A touch screen based exercise roller device comprising:
   an elongated, cylindrical shell configured to support physical activity of a user;
   a processing unit;
   a sensor array for measurement data associated with at least one parameter associated with physical activity, wherein the sensor array linked to the processing unit;
   a touch screen attached onto the outer surface of the shell communicatively linked for controlling a software application, wherein the software application is configured to process data associated with the physical activity of a user; and wherein the sensor array is comprised from at least one of: muscle activity sensors, electromyography sensors, electroencephalography sensors, and electrocardiography sensors.

2. The device of claim 1, wherein the sensor array has at least two sensors for measuring at least one parameter associated with physical activity.

3. The device of claim 1, wherein the sensor array is comprised of at least one pressure sensor.

4. The device of claim 1, wherein measurements from the sensor array are interpreted as signals by the software application.

5. The device of claim 1, wherein the amount of pressure as measured by the sensors in various segments of the sensor array are visually rendered on the touch screen.

6. The device of claim 1, wherein the processing unit is configured to communicate with at least one wearable device.

7. The device of claim 1, wherein the software application comprises a module configured to allow a health care provider to prescribe or customize a regimen for at least one activity associated with physical therapy.

8. The device of claim 1, wherein the software application comprises a module configured to allow a health care provider to prescribe or customize a regimen for at least one activity associated with rehabilitation.

9. The device of claim 1, wherein the software application comprises a module configured to provide a health care provider analyzed and interpreted measured data from physical activity associated with a patient user of the device.

10. The device of claim 1, wherein the software application comprises a module configured to provide a health care provider analyzed and interpreted measured pain data associated with a patient user of the device.

11. The module of claim 10, wherein the module is further configured to provide at least one of: a medical diagnosis, treatment options, prescription of medication, and prescription of a physical therapy regimen.

* * * * *